United States Patent [19]
Harris et al.

[11] Patent Number: 5,327,899
[45] Date of Patent: Jul. 12, 1994

[54] POLYGRAPH AUTOMATED SCORING SYSTEMS

[75] Inventors: John C. Harris, Gaithersburg; Dale E. Olsen, Columbia, both of Md.

[73] Assignee: The Johns Hopkins University, Baltimore, Md.

[21] Appl. No.: 6,916

[22] Filed: Jan. 22, 1993

[51] Int. Cl.$^5$ ............................................. A61B 5/0205
[52] U.S. Cl. ................................ 128/671; 128/734; 128/687; 128/694; 128/716
[58] Field of Search ................. 128/670–671, 128/668, 736, 672, 677–678, 687, 716, 734, 691, 694

[56] References Cited
U.S. PATENT DOCUMENTS

| | | | |
|---|---|---|---|
| 2,538,125 | 1/1951 | Reid | 128/671 |
| 2,944,542 | 7/1960 | Barnett et al. | 128/671 X |
| 3,548,806 | 12/1970 | Fisher | 128/671 |
| 4,887,607 | 12/1989 | Beatty | 128/670 |

Primary Examiner—Angela D. Sykes
Attorney, Agent, or Firm—Francis A. Cooch

[57] ABSTRACT

A polygraph automated scoring system in which polygraph signals are input and a probability of deception is output. To begin the process, digitized polygraph signals are transformed into more fundamental signals. These fundamental signals are then subjected to standardization, a critical step. The standardized signals then have certain features extracted at each question. The features for all of the relevant questions are then standardized against the features for all of the control questions. From each of the resulting standardized relevant features, the 80th percentile is taken. Finally, a logistic regression model (logit) converts this set of 80th percentile features into a probability of deception.

36 Claims, 4 Drawing Sheets

POLYGRAPH AUTOMATED SCORING SYSTEMS

STATEMENT OF GOVERNMENTAL INTEREST

The Government has rights in this invention pursuant to Contract No. N00039-89-C-5301 awarded by the Department of the Navy.

BACKGROUND OF THE INVENTION

On any given day, more than a thousand suspects in criminal investigations will voluntarily take polygraph examinations in the hope of being cleared. The analyses performed are based on the assumption that, when deception is attempted, small changes in human physiology occur as a result of either cognitive processing or emotional stress.

Polygraph tests are administered by more than two thousand trained and experienced examiners in the United States, Canada, Japan India, Israel, Saudi Arabia, Turkey, and many other nations. Somewhere between 40% and 60% of those who take the tests will be cleared on the basis of an examiner's decision of "No deception indicated." For those who are not cleared, the criminal investigative process will continue. Polygraphs affect the lives of many people, from those who are the victims of criminals to those who are suspects.

While the primary use of the polygraph test is during the investigative stage of the criminal justice process, polygraph results are sometimes presented in court as evidence. Polygraph tests also play a small role in parole and probation supervision.

In addition to the significant role in criminal justice, polygraph examinations are also used for national security, intelligence, and counterintelligence activities of the United States and foreign nations. Thousands of federal screening examinations are used annually to grant or deny clearance and access to sensitive operations and material.

A polygraph test format is an ordered combination of relevant questions about an issue, control questions that provide physiological responses for comparison, and irrelevant (or neutral) questions that also provide responses or the lack of responses for comparison, or act as a buffer. All questions asked during a polygraph test are reviewed and discussed with the examinee and reworded when necessary to assure understanding, accommodate partial admissions, and present a dichotomy answerable with a definite "yes" or "no." During the test, the questions are delivered in a monotone voice to avoid emphasis on one question or another.

Polygraph examiners have a choice of several standard test formats. The examiner's decision on which format to use will be based on test objectives, experience, and training.

Three classes of test formats are used: control question tests, concealed knowledge tests, and relevant-irrelevant tests. Each format consists of a prescribed series of questions that together make up a chart. Two to five charts make up a test.

The majority of criminal investigation tests are conducted by using one of the possible formats of control question tests. These tests consist of a series of control, relevant, and irrelevant questions. Each question series is repeated two to five times, and each series produces a separate chart.

An example of a relevant question is, Did you embezzle any of the missing $12,000?. For this test format, the corresponding control questions will be about stealing; the questions are threatening to the subject but are not about the theft at issue. An example is, Before you were employed at this bank, did you ever steal money or property from an employer? The control and relevant questions will be compared.

Irrelevant questions will also be asked that will probably be answered truthfully, are not stressful, and act as buffers. Do you reside in Maryland? or Do they call you Jim? are examples of irrelevant questions.

If the police have facts about a crime that have not become public or common knowledge (facts that would be known to the guilty subject but not to the innocent), they will use a concealed knowledge test. In another version of the concealed knowledge test, the examiner does not know the critical item but believes the examinee does know.

A relevant-irrelevant test differs from a control question test in several ways. It has few, if any, control questions on each chart, the sequence of questions usually varies from chart to chart, and the amplitude of reactions to relevant questions is not compared with the amplitude of reactions to the control questions. This type of test is widely used for multiple-issue testing, such as that used for commercial and counterintelligence screening.

Regardless of the test format used, three physiological measurements are normally recorded:

1. Volumetric measures taken from the upper arm: A standard blood pressure cuff is placed on the arm over the brachial artery and inflated to about 60 mm Hg pressure for an indirect measure of blood pressure variables, together with the strength and rate of pulsation from the heart.
2. Respiratory measures taken from expansion and contraction of the thoracic and abdominal areas using rubber tubes placed around the subject: The resulting data are closely related to the amount of gaseous exchange.
3. Skin conductivity (or resistance) measures of electrodermal activity, largely influenced by eccrine (sweat) gland activity: Electrodes are attached to two fingers of the same hand and a galvanometer records the measured skin conductance or resistance to an electrical current.

When some charts are scored, the examiner cannot make a clear decision and must score the chart as inconclusive. From analyzing charts where decisions were made, a government agency completed a report on polygraph validity based on all the studies of real cases conducted since 1980. Examiner decisions were compared with other results such as confessions, evidence, and judicial disposition. Ten studies, which considered the outcome of 2,042 cases, were reviewed.

It must be pointed out, however, that studies of real polygraph tests are necessarily flawed by the fact that the guilt or innocence of the subject must be determined, and correct calls are more easily confirmed than incorrect calls. For example, if the test shows that the subject is guilty, the examiner will often obtain a confession. Thus, tests scored as guilty are more often confirmed if the subject is guilty.

If the test shows that the subject is innocent, other people may be investigated. If another person is found to be guilty, the test becomes confirmed innocent.

With this in mind, and assuming that every disagreement was a polygraph error, the results in the report indicate an accuracy (or validity) of 98% for the 2,042 confirmed cases. For deceptive cases, the accuracy was also 98%, and for nondeceptive cases, 97%.

Mock-crime studies generally have correct calls about 85% of the time. Because of the nature of mock-crime studies, it is believed that real-crime tests are scored as accurately or more accurately.

The accuracy of polygraph decisions for real cases, then, is somewhere between the 85% demonstrated with mock-crime studies and the 98% demonstrated with confirmed charts.

In 1973, the concept of quantifying polygraph patterns for computer analysis was first presented. Later, analysts at the psychology laboratory at the University of Utah began to develop a computerized scoring algorithm, employing a few of the many variables available in physiological patterns. Their research suggested that the most useful measures were the amplitude and duration of the electrodermal response, the rise and fall of the cardiovascular pattern (related to blood pressure changes), and the length of the respiration tracing within a fixed time sequence. These responses were incorporated into a special-purpose computer analytic system, marketed under the name CAPS (Computer Assisted Polygraph System).

A novel aspect of the CAPS system was the introduction of decisions based on a probability figure. For example, deception might be indicated with a probability of 0.89. The probabilities were developed by using both laboratory and field polygraph data, the latter being tests conducted by the U.S. Secret Service that were confirmed by confession. Two other features of the CAPS system are its ability to rank-order reactions and its analytic system, which gives the greatest weight to electrodermal responses, less to respiratory responses, and the least to cardiovascular responses. Before this work, scoring systems gave equal weight to responses from each of the three physiological recordings.

A deficiency of the CAPS system is that the data are taken from a field polygraph instrument that is often nonlinear, and the analog-to-digital conversion (ADC) is performed after some processing. New instruments will reduce distortions in the data by performing the ADC before any processing, displaying, or printing.

In 1989, Axciton Systems, Inc. of Houston, Tex. developed a new commercial computerized polygraph. This system features a computer that processes the physiological signals directly, scrolls the physiological data across a screen in real time during testing, provides for a later printout, records the test on a hard drive or a floppy disk, and provides a system for ranking subject responses.

The system has been field tested with real cases in a Texas police department and is user friendly. The charts, printed after the test, look like standard polygraph charts and can be hand-scored by traditional methods.

The availability of the Axciton system and the probability of other new computerized polygraphs becoming available requires that new, more accurate algorithms be developed for incorporation in these new systems.

SUMMARY OF THE INVENTION

The basic scoring process of the invention is diagrammed in FIG. 1. In short, polygraph signals are input and a probability of deception is output. Along the way, digitized polygraph signals are transformed into more fundamental signals. These fundamental signals are then subjected to standardization, a critical step. The standardized signals then have certain features extracted at each question. The features for all of the relevant questions are then standardized against the features for all of the control questions. From each of the resulting standardized relevant features, the 80th percentile is taken. A logistic regression model (logit) converts this set of 80th percentile features into a probability of deception.

DETAILED DESCRIPTION

In the preferred embodiment of the invention, the scoring system is designed to work with digitally collected versions of the traditional polygraph, physiological measures: galvanic skin response (GSR), blood pressure (cardio), and respiration (upper only). However, the scoring system of the invention does not use these digitized signals directly but rather it transforms them into more fundamental signals. The purpose of these transformations is to isolate those portions of the signals which contain information about deception so that this information can be better extracted with features. The transformations consist of detrending, baselining, filtering, and taking the derivative. They produce the signals used by the scoring system: detrended GSR, baselined upper respiration, pulse, and blood volume derivative.

Detrending is a technique for removing long-term signal changes unrelated to a particular question. An example of a trend is the drop in the cardio signal caused by a leaking blood pressure cuff. Trends are a cause of the centering adjustments the polygraph examiner makes in the course of an exam. Detrending is accomplished by removing the local mean from each point in the signal. The local mean is calculated from the 30 seconds of data both preceding and following each point.

The cardio and respiration signals each contain two distinctly different kinds of information. The cardio signal has a quickly changing (high frequency) portion corresponding to each pulse and a slowly changing (low frequency) portion corresponding to blood volume. Separating the cardio signal into two signals, the pulse and the blood volume, is accomplished by digital filtering. Likewise, the respiration signal consists of a high frequency portion corresponding to each breath and a low frequency portion corresponding to residual lung volume. Separating the respiration signal is accomplished by baselining.

Figure 1:
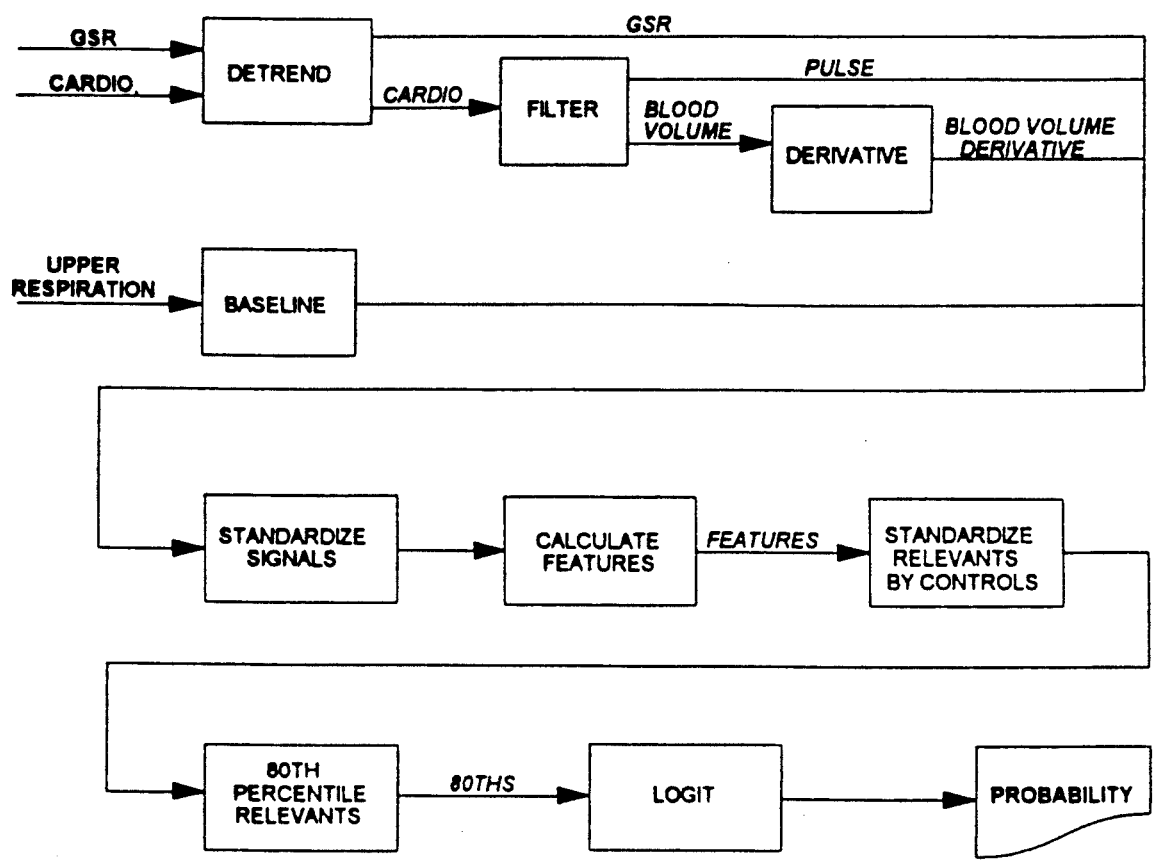
FIG. 1 is a diagram in flow chart format of the automated scoring system of the invention.
Figure 2:
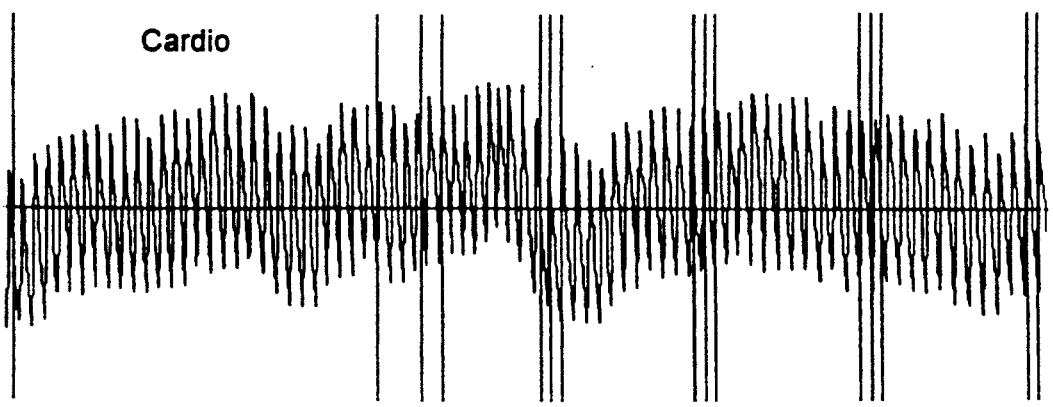
FIG. 2 illustrates a typical blood pressure (cardio) signal obtained during a polygraph exam.
Figure 3:
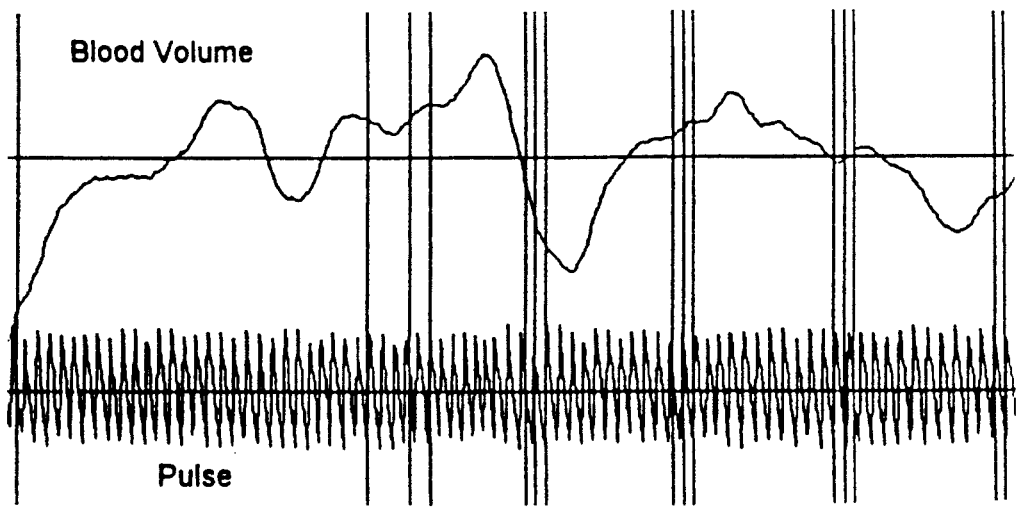
FIG. 3 illustrates the signal of FIG. 2 after being divided by digital filtering into high and low frequency portions.

A typical cardio signal is shown in FIG. 2. Passing it through a Finite Impulse Response (FIR) filter to divide the signal at 4 hertz produces the two signals shown in FIG. 3. Although the scales are somewhat different, it can be seen that the blood volume signal would overlay the middle of the cardio signal and the pulse signal is the movement about this middle.

Figure 4:
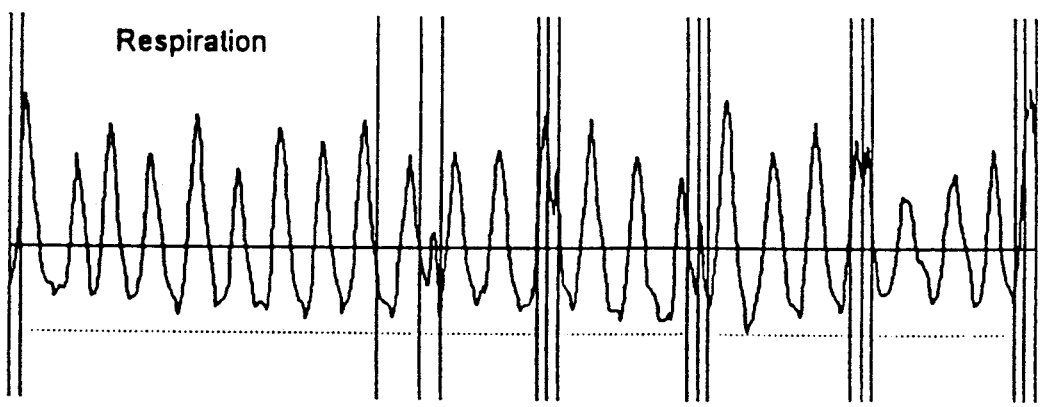
FIG. 4 illustrates a typical respiration signal obtained during a polygraph exam.
Figure 5:
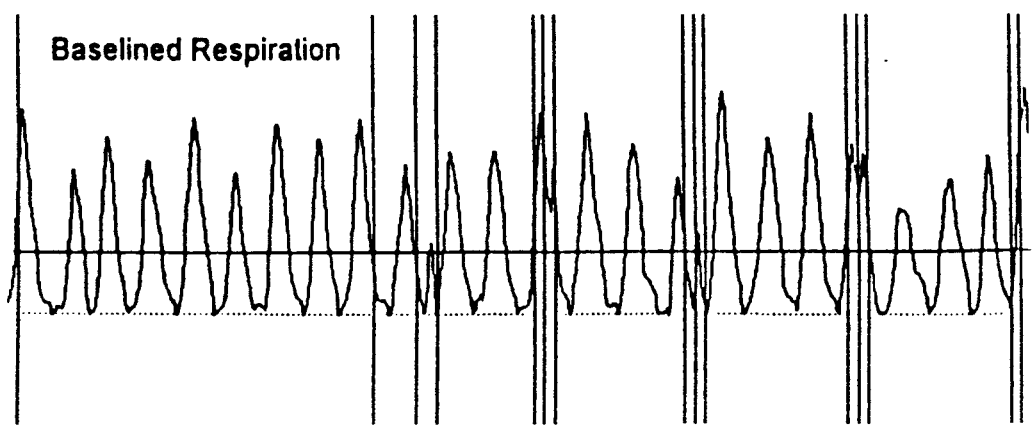
FIG. 5 illustrates the signal shown in FIG. 4 after base-lining.

In the typical respiration signal shown in FIG. 4, the signal moves closer to, then away from the dotted line below it. This movement makes comparing the relative heights of the breaths difficult. Baselining is a technique for equivalencing the breaths. It is done by matching each low point of exhalation between breaths to a common level. FIG. 5 illustrates how baselining flattens the bottom of the signal.

Figure 6:
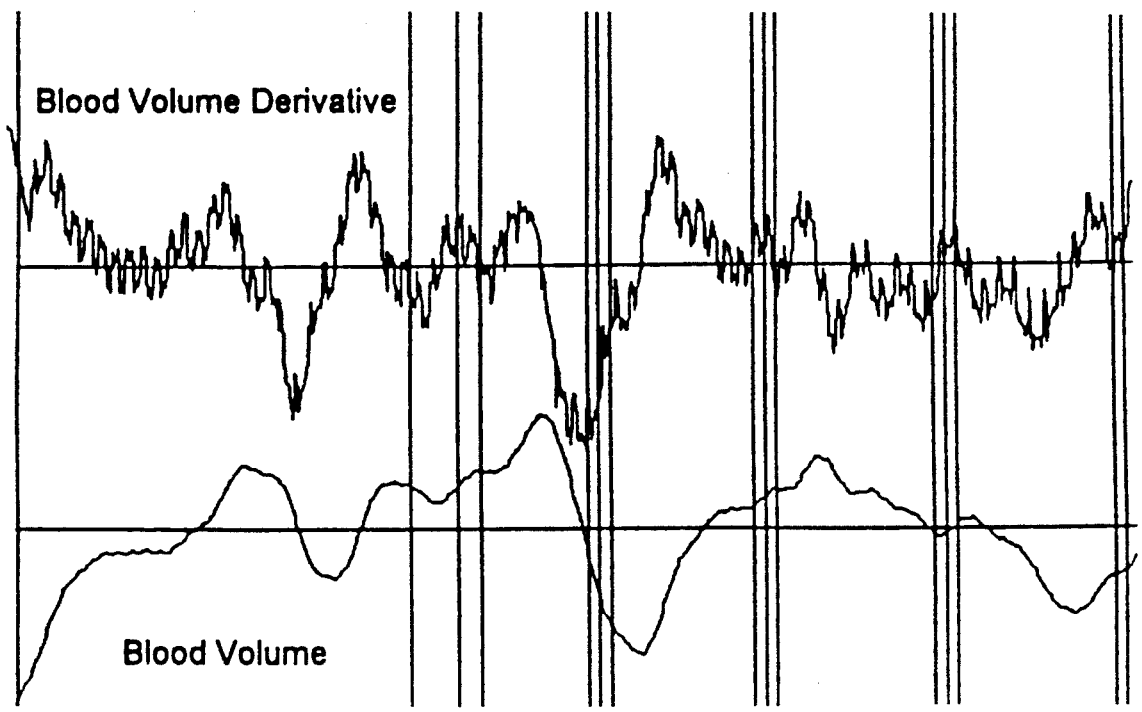
FIG. 6 illustrates the blood volume signal and its derivative.

Sometimes it is important to know not how much something is, but how much it is changing. The derivative of a signal is just such a measure of the rate of change. Shown in FIG. 6 is the blood volume and its derivative. The ragged appearance of the derivative is due to the barely perceptible, but quickly changing, remnants of the pulse. This ragged appearance can be ameliorated through the use of another filter to smooth the pulse remnants out of the blood volume derivative signal.

Figure 7:
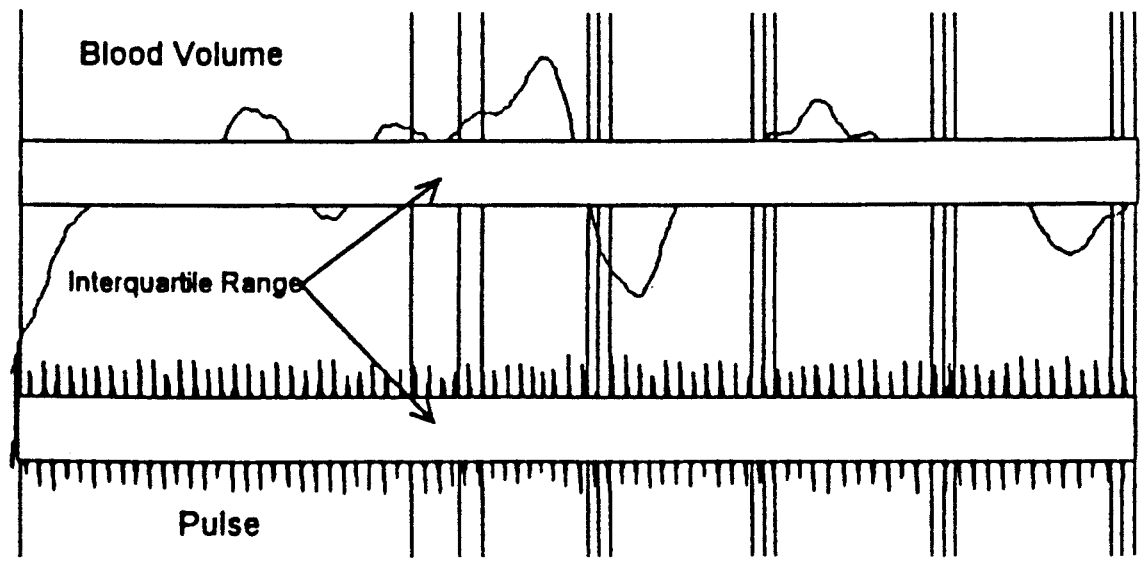
FIG. 7 illustrates the use of the interquartile range to standardize the pulse and blood volume signals.

Signal standardization allows the amplitude measurements from different individuals, or different charts from one individual, to be scored using a common scoring system. The typical method of standardization uses the mean and standard deviation of each signal for standardizing that signal. However, this method is inaccurate when the signal contains artifacts such as movements or deep breaths. So instead, the invention uses the interquartile range to standardize. This may be thought of as a band which if covering the center of the signal, would allow only half the signal to show. One-fourth of the signal would be above the band and one-fourth below it. The edges of the band correspond to the 25th and 75th percentiles (1st and 3rd quartiles, respectively) and the width of this band is the interquartile range. After standardization, every signal has a band exactly the same width. Examples are shown in FIG. 7.

Features are the means by which signal information is changed into question information. After each question, a characteristic of the signal is computed for a certain period of time. This period of time is referred to as the response window. The response windows begin and end at different times for different signals and the features used are also different. The scoring system of the invention uses the features as shown in Table 1 below,

TABLE 1

Figure 8:
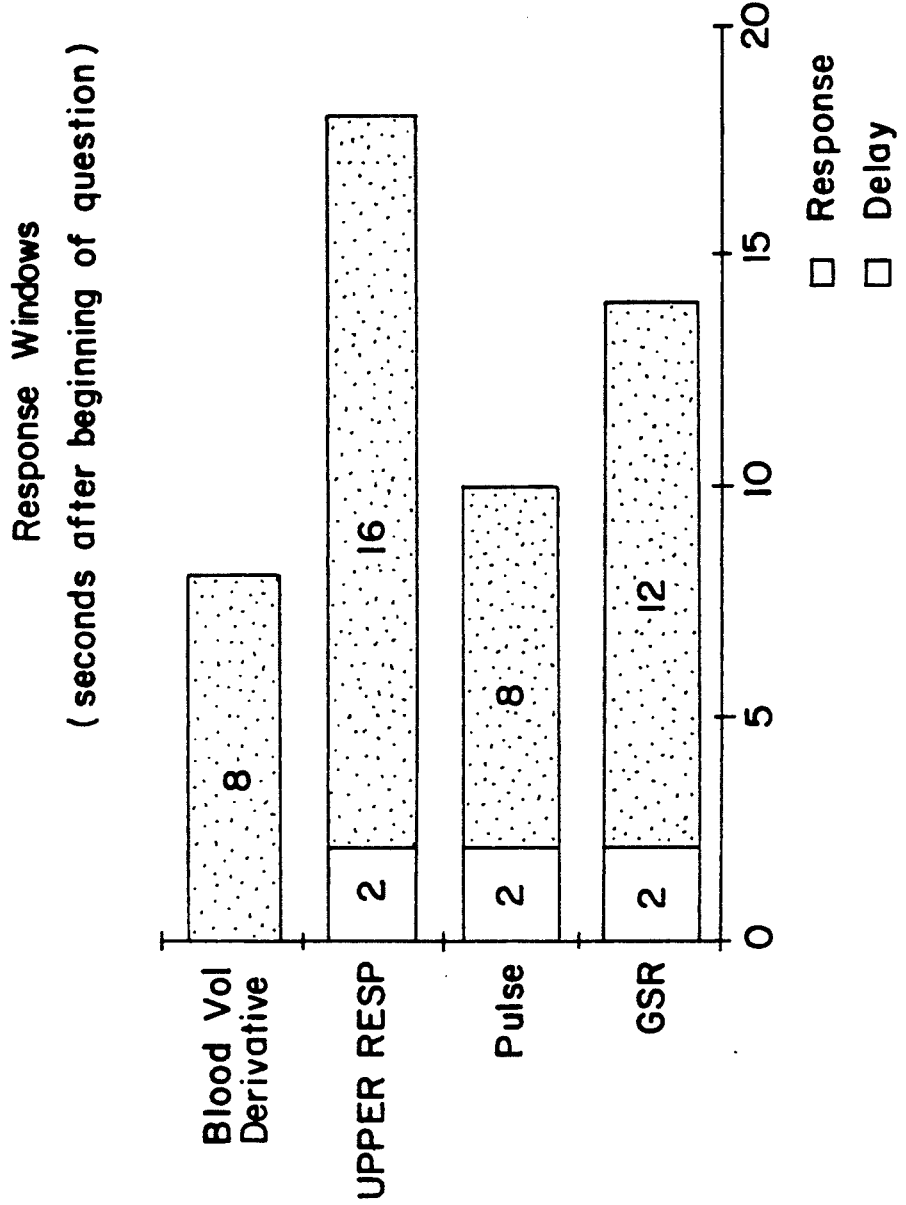
FIG. 8 illustrates the response window used to compute features for signals of interest to the invention.

| Signal | Feature |
|---|---|
| GSR | Range |
| Pulse | Line Length |
| Upper Respiration | 80th Percentile |
| Blood Volume Derivative | 75th Percentile |
| Pulse | 55th Percentile | and the response windows as shown in FIG. 8.

The percentile features (80th, 75th and 55th) represent the amplitude that the signal was at or below during the response window for the indicated amount of time (80%, 75% and 55%). The range is the maximum amplitude minus the minimum amplitude that the signal attained during the period of time being measured. The line length feature is a measure of change which is sensitive to both a lot of small changes and a few large ones.

The basis for scoring is the subject's reaction to the relevant questions relative to that of the controls. This relative comparison is achieved by standardizing the relevants to the controls. This is done by calculating the mean of the controls and the joint control and relevant standard deviation. The joint standard deviation is the variability of the controls about their mean and the relevants about their mean. The joint standard deviation is used because of the statistically small number of questions asked in an exam. Thus, $$R_i' = \frac{R_i - \mu_C}{\sigma_{CR}}$$

where $R_i$ is the feature value for the ith relevant question, $\mu_c$ is the mean of the control questions, $\sigma_{CR}$ is the joint standard deviation of the control and relevant questions and $R_i'$ is the standardized feature value for the ith relevant question.

The information about many relevant (and control) questions must be reduced to information about an entire exam. This is done by finding the 80th percentile value of each standardized relevant feature, the 80th percentile being computed by linear interpolation. For example, if an exam has eleven relevant questions, the ninth largest response for each feature is used. This technique strikes the proper balance between sensitivity to deception and false indications due to artifacts or other random factors.

Information from all of the signals and features must be analyzed to discriminate between deceptive and nondeceptive subjects. This can be done through the use of a neural net or by statistical discriminant analysis. However, in the preferred embodiment, to determine deception, the information is combined by a logistic regression model. To produce a probability of deception, it weights each signal/feature as follows: GSR—49%, Blood Volume Derivative—21%, Upper Respiration—16%, and Pulse—14%.

The form of the logistic regression is:

$$P(\text{deception}) = \frac{e^{score}}{1 + e^{score}}$$

where:

score = $\omega_1 \cdot$ GSR Range
+
$\omega_2 \cdot$ Pulse Line Length
+
$\omega_3 \cdot$ Upper Respiration 80th Percentile
+
$\omega_4 \cdot$ Blood Volume Derivative 75th Percentile
+
$\omega_5 \cdot$ Pulse 55th Percentile
+
$\beta$ (the intercept with a value of $-6.0168$)

As shown in Table 2, the signs of the weights ($\omega$'s) show whether an increase (positive sign) or a decrease (negative sign) in a feature is associated with deception.

TABLE 2

| Feature | Weigths | Direction |
|---|---|---|
| GSR Range | 5.5095 | Increase |
| Pulse Line Length | −2.0866 | Decrease |
| Upper Respiration 80th Percentile | −2.5954 | Decrease |
| Blood Volume Derivative 75th Percentile | 3.0643 | Increase |

TABLE 2-continued

| Feature | Weigths | Direction |
|---|---|---|
| Pulse 55th Percentile | 2.1633 | Increase |

A related procedure (double logit), compares relevants to controls and reduces information, not by standardizing and using the 80th percentile, but, in one step, by using an initial series of logits, one for each feature used in the final logit.

For a particular question sequence, the series of logits can be viewed as shown in Table 3.

TABLE 3

| | Format and feature-vector display for the control question test analyzed. | | | | | | | | | | |
|---|---|---|---|---|---|---|---|---|---|---|---|
| Logit | Questions on Chart K | | | | | | | | | | |
| computed | N | R | N | C | R | N | C | R | N | C | R |
| score | 1 | 2 | 3 | 4 | 5 | 6 | 7 | 8 | 9 | 10 | 11 |
| Score$_1$, for Feature 1 | $X_{1,1}$ | $X_{1,2}$ | . | . | . | . | . | . | . | $X_{1,10}$ | $X_{1,11}$ |
| Score$_2$, for Feature 2 | $X_{2,1}$ | $X_{2,2}$ | . | . | . | . | . | . | . | $X_{2,10}$ | $X_{2,11}$ |
| . | . | . | . | . | . | . | . | . | . | . | . |
| Score$_5$, for Feature 5 | $X_{5,1}$ | $X_{5,2}$ | . | . | . | . | . | . | . | $X_{5,10}$ | $X_{5,11}$ |

The scores can now be combined by the final logit to produce a probability of deception.

We claim:

1. A method for automatically scoring by computer a polygraph test comprised of a plurality of relevant and control questions, the polygraph test generating a plurality of digitized physiological signals, the method comprising the steps of:
    transforming the digitized signals into a plurality of fundamental signals;
    standardizing the fundamental signals;
    extracting a plurality of features from the standardized fundamental signals at each question;
    standardizing the features for all relevant questions against the features for all control questions;
    determining an 80th percentile value of each standardized relevant feature; and
    combining the 80th percentile values to produce a probability of deception.

2. The polygraph scoring method as recited in claim 1, wherein the plurality of digitized physiological signals represent galvanic skin response (GSR), blood pressure and respiration.

3. The polygraph scoring method as recited in claim 2, the transforming step comprising the steps of:
    detrending the GSR signal;
    dividing the blood pressure signal into a high frequency portion representing a pulse and into a low frequency portion representing a blood volume;
    baselining the respiration signal; and
    measuring the rate of change of the blood volume signal.

4. The polygraph scoring method as recited in claim 3, the detrending step comprising the steps of:
    calculating a local mean from 30 seconds of data both preceding and following each point in the GSR signal; and
    removing the calculated local mean from each point in the GSR signal.

5. The polygraph scoring method as recited in claim 3, the dividing step comprising the step of passing the blood pressure signal through a Finite Impulse Response filter at four hertz.

6. The polygraph scoring method as recited in claim 3, the baselining step comprising the step of matching each low point of exhalation between breaths to a common level.

7. The polygraph scoring method as recited in claim 3, the measuring step comprising the step of taking the derivative of the blood volume signal.

8. The polygraph scoring method as recited in claim 3, the extracting step comprising the step of computing a characteristic of each standardized, fundamental signal for a specific period of time.

9. The polygraph scoring method as recited in claim 8, the computing step comprising the steps of:
    calculating the range for the GSR signal, the range being the maximum amplitude minus the minimum amplitude that the signal attained during the period of time;
    calculating a line length for the pulse signal, the line length being the measure of change which is sensitive to both a lot of small changes and a few large ones;
    calculating the 55th percentile for the pulse signal, the 55th percentile being the amplitude that the signal was at or below during the period of time for 55% of the time;
    calculating the 80th percentile for the upper respiration signal, the 80th percentile being the amplitude that the signal was at or below during the period of time for 80% of the time; and
    calculating a 75th percentile for the rate of change of the blood volume signal, the 75th percentile being the amplitude that the signal was at or below during the period of time for 75% of the time.

10. The polygraph scoring method as recited in claim 9, wherein the period of time for calculating the range for the GSR signal is 11 seconds, the period beginning two seconds after the beginning of the question.

11. The polygraph scoring method as recited in claim 9, wherein the period of time for calculating the line length for the pulse signal is 8 seconds, the period beginning two seconds after the beginning of the question.

12. The polygraph scoring method as recited in claim 9, wherein the period of time for calculating the 80th percentile for the upper respiration signal is 16 seconds, the period beginning two seconds after the beginning of the question.

13. The polygraph scoring method as recited in claim 9, wherein the period of time for calculating the 75th percentile for the rate of change of the blood signal is 8 seconds, the period beginning with the beginning of the question.

14. The polygraph scoring method as recited in claim 3, the standardizing the features step comprising the steps of:
    calculating the mean of the control questions; and
    calculating the joint standard deviation of the control questions and the relevant questions, wherein the joint standard deviation is the variability about the mean of the control questions and the variability about the mean of the relevant questions.

15. The polygraph scoring method as recited in claim 14, wherein the standardization for each feature for the ith relevant question is computed using the formula:

$$R_i' = \frac{R_i - \mu_C}{\sigma_{CR}}$$

wherein $R_i$ is the feature value for the ith relevant question, $\mu_c$ is the mean of the control questions, $\sigma_{CR}$ is the joint standard deviation of the control and relevant questions, and $R_i$ is the standardized feature value for the ith relevant question.

16. The polygraph scoring method as recited in claim 3, wherein a logistic regression model is used to combine the 80th percentile values of the standardized relevant features.

17. The polygraph scoring method as recited in claim 16, wherein the logistic regression model has the form:

$$P(\text{deception}) = \frac{e^{score}}{1 + e^{score}}$$

where:

$score = \omega_1 \cdot $ GSR Range
    $+$
    $\omega_2 \cdot $ Pulse Line Length
    $+$
    $\omega_3 \cdot $ Upper Respiration 80th Percentile
    $+$
    $\omega_4 \cdot $ Blood Volume Derivative 75th Percentile
    $+$
    $\omega_5 \cdot $ Pulse 55th Percentile
    $+$
    $\beta$ 18. The polygraph scoring method as recited in claim 2, the standardizing the fundamental signals step comprising the step of selecting an interquartile range of the signals, the interquartile range corresponding to a band having a width defined by the 1st and 3rd quartiles or the 25th and 75th percentiles, respectively.

19. A method for automatically scoring by computer a polygraph test, the polygraph test generating a plurality of digitized physiological signals, the method comprising the steps of:
    extracting ia plurality of features from the digitized signals; and
    using a logistic regression model to compute a probability of deception from the features.

20. A method for automatically scoring by computer a polygraph test comprised of a plurality of relevant and control questions, the polygraph test generating a plurality of digitized physiological signals, the method comprising the steps of:
    transforming the digitized signals into a plurality of fundamental signals;
    standardizing the fundamental signals;
    extracting a plurality of features from the standardized fundamental signals at each question;
    using a plurality of logistic regression models to simultaneously compare the relevant questions to the control questions and combine the same feature from all questions to compute a score for each feature; and
    using a final logistic regression model to combine the scores of the features to produce a probability of deception.

21. A method for automatically scoring a polygraph test comprised of a plurality of relevant and control questions, the polygraph test generating a plurality of digitized physiological signals, the method comprising the steps of:
    transforming the digitized signals into a plurality of fundamental signals;
    extracting a plurality of features from the fundamental signals at each question;
    standardizing the features for the relevant questions against the features for the control questions;
    determining a percentile value of each standardized relevant feature; and
    analyzing the percentile values to produce a probability of deception.

22. The method as recited in claim 21, further comprising the step of standardizing the fundamental signals, the standardizing the fundamental signals step following the transforming step.

23. The method as recited in claim 22, wherein the analyzing step comprises the step of combining the percentile values to produce a probability of deception.

24. The method as recited in claim 23, wherein the percentile value of each standardized relevant feature is an 80th percentile.

25. The method as recited in claim 23, wherein the plurality of digitized physiological signals represent galvanic skin response (GSR), blood pressure and respiration.

26. The method as recited in claim 25, the transforming step comprising the steps of:
    detrending the GSR signal;
    dividing the blood pressure signal into a high frequency portion representing a pulse and into a low frequency portion representing a blood volume;
    baselining the respiration signal; and
    measuring the rate of change of the blood volume signal.

27. The method as recited in claim 26, the detrending step comprising the steps of:
    calculating a local mean from data both preceding and following each point in the GSR signal; and
    removing the calculated local mean from each point in the GSR signal.

28. The method as recited in claim 26, the dividing step comprising the step of passing the blood pressure signal through a Finite Impulse Response filter.

29. The method as recited in claim 26, the baselining step comprising the step of matching each low point of exhalation between breaths to a common level.

30. The method as recited in claim 26, the measuring step comprising the step of taking the derivative of the blood volume signal.

31. The method as recited in claim 26, the extracting step comprising the step of computing a characteristic of each standardized, fundamental signal for a specific period of time.

32. The method as recited in claim 31, the computing step comprising the steps of:
    calculating the range for the GSR signal, the range being the maximum amplitude minus the minimum amplitude that the signal attached during the period of time;
    calculating a line length for the pulse signal, the line length being the measure of change which is sensitive to both a lot of small changes and a few large ones;
    calculating a percentile for the pulse signal, the percentile being the amplitude that the signal was at or below during the period of time for a portion of the time equal to the percentile;

calculating a percentile for the upper respiration signal, the percentile being the amplitude that the signal was at or below during the period of time for a portion of the time equal to the percentile; and calculating a percentile for the rate of change of the blood volume signal, the percentile being the amplitude that the signal was at or below during the period of time for a portion of the time equal to the percentile.

33. The method as recited in claim 23, wherein a logistic regression model is used to combine the percentile values of the standardized relevant features.

34. The method as recited in claim 22, the standardizing the fundamental signals step comprising the step of selecting an interquartile range of the signals.

35. The method as recited in claim 34, wherein the interquartile range corresponds to a band having a width defined by the 1st and 3rd quartiles or the 25th and 75th percentiles, respectively.

36. The method as recited in claim 21, the standardizing the features step comprising the steps of:
calculating the mean of the control questions; and
calculating the joint standard deviation of the control questions and the relevant questions, wherein the joint standard deviation is the variability about the mean of the control questions and the variability about the mean of the relevant questions.

* * * * *

UNITED STATES PATENT AND TRADEMARK OFFICE
CERTIFICATE OF CORRECTION

PATENT NO. : 5,327,899
DATED : July 12, 1994
INVENTOR(S) : John C. Harris and Dale E. Olsen It is certified that error appears in the above—identified patent and that said Letters Patent is hereby corrected as shown below:

Column 8, line 40, delete "11" and substitute therefor -- 12 --.

Column 9, line 44, delete "ia" and substitute therefor -- a --.

Column 10, line 59, delete "attached" and substitute therefor -- attained --.

Signed and Sealed this

Sixth Day of December, 1994

Attest:

BRUCE LEHMAN

*Attesting Officer*   *Commissioner of Patents and Trademarks*